US010221134B2

(12) United States Patent
Wang et al.

(10) Patent No.: US 10,221,134 B2
(45) Date of Patent: Mar. 5, 2019

(54) PROCESSES TO PRODUCE BRIVARACETAM

(71) Applicant: ESTEVE QUIMICA S.A., Barcelona (ES)

(72) Inventors: Peng Wang, Scotch Plains, NJ (US); Pixu Li, Suzhou (CN); Qiang Wei, Suzhou (CN); Yuanhua Liu, Suzhou (CN)

(73) Assignee: Esteve Quimica S.A., Barcelona (ES)

( * ) Notice: Subject to any disclaimer, the term of this patent is extended or adjusted under 35 U.S.C. 154(b) by 0 days.

(21) Appl. No.: 15/575,373

(22) PCT Filed: May 24, 2016

(86) PCT No.: PCT/US2016/033965
§ 371 (c)(1),
(2) Date: Nov. 19, 2017

(87) PCT Pub. No.: WO2016/191435
PCT Pub. Date: Dec. 1, 2016

(65) Prior Publication Data
US 2018/0155284 A1   Jun. 7, 2018

(30) Foreign Application Priority Data

| May 25, 2015 | (CN) | ............ 2015 1 0271449 |
| Jul. 21, 2015 | (CN) | ............ 2015 1 0430387 |
| Oct. 10, 2015 | (CN) | ............ 2015 1 0648574 |
| Feb. 24, 2016 | (CN) | ............ 2016 1 0099672 |

(51) Int. Cl.
| C07D 207/27 | (2006.01) |
| A61K 31/4015 | (2006.01) |
| C07C 53/19 | (2006.01) |
| C07C 53/50 | (2006.01) |
| C07C 67/307 | (2006.01) |
| C07C 69/63 | (2006.01) |
| C07C 71/00 | (2006.01) |
| C07C 209/08 | (2006.01) |
| C07C 231/14 | (2006.01) |
| C07C 233/05 | (2006.01) |
| C07C 237/06 | (2006.01) |

(52) U.S. Cl.
CPC ........ *C07D 207/27* (2013.01); *A61K 31/4015* (2013.01); *C07C 53/19* (2013.01); *C07C 53/50* (2013.01); *C07C 67/307* (2013.01); *C07C 69/63* (2013.01); *C07C 71/00* (2013.01); *C07C 209/08* (2013.01); *C07C 231/14* (2013.01); *C07C 233/05* (2013.01); *C07C 237/06* (2013.01)

(58) Field of Classification Search
CPC .................................................. C07D 207/27
See application file for complete search history.

(56) References Cited

U.S. PATENT DOCUMENTS

| 2008/0009638 A1 | 1/2008 | Surtees et al. |
| 2009/0318708 A1 | 12/2009 | Ates et al. |
| 2012/0021469 A1* | 1/2012 | Gooding ............... C12N 9/80 435/121 |
| 2014/0031368 A1 | 1/2014 | Breslow et al. |
| 2014/0228579 A1 | 8/2014 | Nikonov et al. |

FOREIGN PATENT DOCUMENTS

| KR | 20070081959 A | 2/2009 |
| WO | 200162726 A2 | 8/2001 |
| WO | WO 01/62726 A2 † | 8/2001 |
| WO | 2009022839 A2 | 2/2009 |
| WO | WO 2009/022839 A2 † | 2/2009 |
| WO | 2012140504 A1 | 10/2012 |

OTHER PUBLICATIONS

B.M. Kenda et al., Discovery of Substituted Pyrrolidone Butanamides as New Agents with Significant Antiepileptic Activity, J. Med. Chem. 2004, 47, No. 3, 530-549.
Discovery of 4-Substituted Pyrrolidone Butanamides as New Agents with Significant Antiepileptic Activity.†

\* cited by examiner
† cited by third party

*Primary Examiner* — Rebecca L Anderson
*Assistant Examiner* — Karen Cheng
(74) *Attorney, Agent, or Firm* — VLP Law Group LLP; Kent H. Cheng (57) ABSTRACT

The present invention provides a scalable synthesis of enantiomerically pure brivaracetam, and related derivatives.

11 Claims, 2 Drawing Sheets

PROCESSES TO PRODUCE BRIVARACETAM

CROSS-REFERENCE TO RELATED APPLICATIONS

The present application claims priority to the following Chinese Patent Applications: 201510271449.6 filed May 25, 2105; 201510430387.9 filed Jul. 21, 2015; 201510648574.4 filed Oct. 10, 2015; and 201610099672.1 filed Feb. 24, 2016, the entire contents of which are incorporated herein by reference.

BACKGROUND OF THE INVENTION

1. Field of the Invention

The present invention relates to a compound (formula XII, brivaracetam) and a method for preparing formula XII, which is a new generation of antiepileptic drug found by screening for ligands with a higher affinity for LBS than levetiracetam. LBS is a unique brain-specific Levetiracetam (LEV) binding site that is correlated with anticonvulsant effects in animal models of epilepsy.

XII

Brivaracetam

2. Description of the Related Art

Epilepsy is one of the most common neurological disorders, affecting about 1 of the population worldwide. With currently available antiepileptic drugs (AEDs), one-third of patients continue to suffer from seizures even when treated at maximally tolerated dosages, either in monotherapy or in various drug combinations. Pharmacoresistance is associated with physical risks, reduced life expectancy, reduced quality of life and impairments in social opportunities. The acetamide derivate Levetiracetam (LEV) that primarily targets the synaptic vesicle protein 2A has been one of the most successful second-generation antiepileptic drugs. But irritability and other psychiatric adverse effects, such as depression, anger, and even psychosis, have been a "handicap" with Levetiracetam.

Brivaracetam is a Levetiracetam analog. Brivaracetam has an advantage over Levetiracetam in that it gets into the brain "much more quickly," which means that "it could be used for status epilepticus, or acute seizures that cluster, or prolonged seizures". From the Phase III trials, the self-reported rate of irritability with Brivaracetam was 2% for both drug doses (100 mg and 200 mg) vs 1% for placebo, which compares to as much as 10% for levetiracetam in some postmarketing studies.

With the improved safety profile and possibility to be used for wider range of epilepsy, Brivaracetam is considered as one of the most promising 3rd-generation anti-epileptic drugs.

Typically, a diastereomeric mixture of (2S)-2-[(4R)-2-oxo-4-propylpyrrolidin-1-yl]-butanamide and (2S)-2-[(4S)-2-oxo-4-propylpyrrolidin-1-yl]-butanamide (Brivaracetam) is synthesized and it is purified by chiral HPLC (U.S. Pat. Nos. 6,784,197, 7,629,474) (Scheme 1-1)—resulting in the problem of low yield.

U.S. Pat. No. 8,957,226 (Example 1, 3) and U.S. Pat. No. 8,338,621 (Example 4, 11), disclosed two routes to synthesize brivaracetam, which also have the same problem (Scheme 1-2).

The problem is the same in the process disclosed by the report of Kenda et al. (Journal of Medicinal Chemistry, 2004, 47, 530) (Scheme 1-3).

Technical Problem: To date, there is no enantioselective synthesis of brivaracetam. No scalable synthesis of enantiomerically pure brivaracetam without chiral column chromatography purification. The current processes to brivaracetam require tedious purification, significant loss of material, and high equipment investment.

There is a need to develop a cost effective method for the preparation of brivaracetam without chiral HPLC separation. The new preparation method should be applicable to the large-scale synthesis.

SUMMARY OF THE INVENTION

It is the object of the present invention to provide a stereoselective and cost effective method for the preparation of brivaracetam, (2S)-2-[(4R)-2-oxo-4-propylpyrrolidin-1-yl]butanamide, with high enantiomeric purity.

One purpose of the present application is to provide a key intermediate, compound of formula IV, and its preparation.

A further purpose of the present application is to provide a method to prepare other key intermediates of Brivaracetam from the compound of formula IV.

Another purpose of the present application is to provide a process for the synthesis of the compound of formula XII (Brivaracetam) from the compound of formula IV.

The present application provides a compound of formula IV:

wherein R is C1-20 saturated or unsaturated alkyl or C1alkyl-unsubstituted or substituted alkylaryl. Preferably, R represents a substituent group selected from methyl, ethyl, propyl, isopropyl, allyl, butyl, isobutyl, tert-butyl, n-pentyl, n-hexyl, and benzyl. More preferably, wherein R represents a substituent group selected from methyl, ethyl, tert-butyl, and benzyl.

Moreover, the n-propyl at the 4-position of the compound of formula IV requires only the (R) configuration, and the configuration at 3-position of the ester group has no specific requirements, so the carbon center 3-position can be (R) or (S) configuration, or a mixture of both.

The present application provides a process for the preparation of the compound of formula IV:

wherein R is saturated or unsaturated C1-20 alkyl or C1alkyl-unsubstituted or substituted aryl. Preferably, R represents a substituent group selected from methyl, ethyl, propyl, isopropyl, allyl, butyl, isobutyl, tert-butyl, n-pentyl, n-hexyl, and benzyl. More preferably, wherein R represents a substituent group selected from methyl, ethyl, tert-butyl, and benzyl.

The process of preparing the compound of formula IV from the compound of formula III by ring-opening is conducted in the presence of a ethyl metallic reagent and an aprotic solvent. More specifically, the ethyl metallic reagent is selected from the group consisting of EtMgBr, EtMgCl, EtLi, and mixtures thereof, and the process is preferably conducted in the presence of CuX or CuCN.

In a specific embodiment, the reaction is carried out at a temperature of −78 to 200° C. The ethyl metallic reagent is from about 1 to about 5 mole equivalent. Preferably the ethyl metallic reagent is one or more form EtMgBr, EtMgCl, and EtLi. More preferably, the ethyl metallic reagent is combined with CuX or CuCN, which is present at 0.01 to 2 mole equivalent. Preferably, the solvent is one or more of the following: tetrahydrofuran, 2-methyl tetrahydrofuran, toluene, dichloromethane, ethyl ether and methyl tert-butyl ether.

A further purpose of the present application is to provide a method to prepare key intermediates of the compound of formula XII (Brivaracetam) from the compound of formula IV.

In a specific embodiment, the compound of formula VI can be prepared from compound IV, and the compound VI is a key intermediate of the compound of formula XII (Brivaracetam), wherein, R is saturated or unsaturated C1-20 alkyl or C1alkyl-unsubstituted or substituted alkylaryl.

In a specific embodiment, the reaction of compound of formula IV to compound of formula VI is conducted in a solvent with salt or base. The reaction is carried out at a temperature of from about 50 to about 200° C. The salt or base is from about 1 to about 5 mole equivalent. Preferably, wherein the salt selected from in one or more of lithium chloride, sodium chloride, potassium chloride, magnesium chloride, or magnesium bromide, the base selected from in one or more of lithium hydroxide, potassium hydroxide or sodium hydroxide. the solvent selected from in one or more of N-methyl pyrrolidone, the N,N-dimethylformamide, dimethyl sulfoxide, sulfolane, and 4-methyl-2-pentanol;

or, if R contains unsaturation, such compounds of formula IV converted by first removing the R group with metal catalyst, and then decarboxylation reaction at a temperature in the range 25° C. to 200° C. to give a compound of formula VI. Preferably, wherein the solvent selected from in one or more of toluene, methyl tert-butyl ether, N-methyl pyrrolidone, N,N-dimethylformamide, dimethyl sulfoxide.

Regarding the metal catalyst, as common knowledge, the use of the metal catalyst may be carried out by known methods and the catalyst may be a Pd, Pt, Ni, triphenylphosphine palladium, et.al. The selection of the catalyst, and the specific method of use are disclosed in 'Protective Groups in Organic Synthesis, Third Edition.' Theodora W. Greene, Peter G M Wuts, 1999, John Wiley & Sons, Inc., Chapter 5, and so on.

Another purpose of the present application is to provide the following process for the synthesis of compounds of formula XII (Brivaracetam) from the compound of formula IV.

wherein, R is saturated or unsaturated C1-20 alkyl or C1alkyl-unsubstituted or substituted aryl. Preferably, wherein R represents a substituent group selected from methyl, ethyl, propyl, isopropyl, allyl, butyl, isobutyl, tert-butyl, n-amyl, n-hexyl, benzyl. More preferably, wherein R represents a substituent group selected from methyl, ethyl, tert-butyl, benzyl.

R1 is saturated or unsaturated C1-20 alkyl or C1alkyl-unsubstituted or substituted aryl. Preferably, wherein R1 represents a substituent group selected from methyl, ethyl, propyl, isopropyl, allyl, butyl, isobutyl, tert-butyl, n-pentyl, n-hexyl, benzyl. More preferably, wherein R1 is ethyl. X is Cl, Br, I, OMs, OTs, or ONs. Preferably, X is Br.

As common knowledge, according to the type of reaction, R, R1 or X may be selectively chosen. For example, R may be a C1-20 hydrocarbon group without affecting any decarboxylation; R1 may be capable of forming an arbitrary ring-opening C1-6 alkyl ester, depending on the alcohol used in the ring-opening reaction; and X may be any leaving group such as Cl, Br, I, OMs, OTs, ONs.

In a specific embodiment, R may be methyl, ethyl, propyl, allyl, n-butyl, iso-butyl, isopropyl, n-pentyl, n-hexyl, t-butyl or benzyl.

In a specific embodiment, R and R1 may be ethyl, and X may be Br.

The preparation method of brivaracetam and intermediate compounds obtained during the process is described below. The present invention may be embodied in many different forms and should not be construed as being limited to the description set forth herein.

In a specific embodiment, the reaction conditions for each reaction step are detailed below:

Synthesis the Compound of Formula IV from the Compound of Formula III:

The reaction from the compound of formula III and ethyl metallic reagent, in aprotic solvent, to synthesize the compound of formula IV. The reaction is carried out at a temperature of from about −78 to about 200° C. The ethyl metallic reagent is present from about 1 to about 5 mole equivalents. Preferably the ethyl metallic reagent is one or more form EtMgBr, EtMgCl, or, EtLi. More preferably, the ethyl metallic reagent is combined with CuX or CuCN, which is present from about 0.01 to about 2 mole equivalents. The aprotic solvent is one or more from tetrahydrofuran, 2-methyl tetrahydrofuran, toluene, dichloromethane, ethyl ether and methyl tert-butyl ether.

Synthesis the Compound of Formula VI from the Compound of Formula IV:

The reaction from compound of formula IV to compound of formula VI is conducted in solvent with a salt or base. The reaction is carried out at a temperature of from about 50 to about 200° C. The salt or base is from about 1 to about 5 mole equivalents. Preferably, the salt is selected from one or more of lithium chloride, sodium chloride, potassium chloride, magnesium chloride, and magnesium bromide. The base is selected from one or more of lithium hydroxide, potassium hydroxide or sodium hydroxide. The solvent is selected from one or more of N-methyl pyrrolidone, the N,N-dimethylformamide, dimethyl sulfoxide, sulfolane, and 4-methyl-2-pentanol.

Alternatively, if R contains unsaturation, such compounds of formula IV by first removing the R group by metal catalyst, and then decarboxylation reaction at a temperature in the range 25° C. to 200° C. to give a compound of formula VI. Preferably, the solvent is selected from in one or more of toluene, methyl tert butyl ether, N-methyl pyrrolidone, N,N-dimethylformamide, dimethyl sulfoxide.

Synthesis the Compound of Formula VII from the Compound of Formula VI:

The reaction of compound of formula VI to compound of formula VII is preferably conducted in solvent 1 with TMSI, TMSBr, HBr, HCl or HI.

Alternatively, the compound of the formula VI undergoes ring opening and hydrolysis under basic conditions, and in a solvent 1 with MsCl, TsCl, or NsCl, to obtain compounds of formula VII.

The solvent 1 is one or more of N-methyl pyrrolidone, the N,N-dimethylformamide, dimethyl sulfoxide, sulfolane, dichloromethane, acetonitrile or C1-20 hydrocarbyl alcohols. Basic hydrolysis uses sodium hydroxide, potassium hydroxide, or lithium hydroxide.

Synthesis the Compound of Formula IX from the Compound of Formula VII:

The reaction from the compound of formula VII and (S)-2-aminobutanamide or its salt, in solvent, under basic conditions, at a temperature in the range 25° C. to 200° C. to synthesize the compound of formula IX. The base is from about 1 to about 5 mole equivalents, (S)-2-aminobutanamide or its salt is from about 0.5 to about 5 mole equivalents. Preferably, the base is selected from one or more of sodium hydroxide, potassium hydroxide, sodium carbonate, potassium carbonate, sodium hydride, sodium t-butoxide, potassium tert-butoxide, LDA, LiHMDS or NaHMDS. The solvent is selected from one or more of N-methyl pyrrolidone, the N,N-dimethylformamide, dimethyl sulfoxide, or sulfolane.

Synthesis the Compound of Formula XII from the Compound of Formula IX:

The reaction from the compound of formula IX, is conducted in a solvent, at a temperature in the range 25° C. to 200° C. to synthesize the compound of formula XII. Preferably, HOBt or 2-hydroxypyridine is used to promote the reaction. The solvent is selected from in one or more of toluene, methyl isobutyl ketone, xylene, or chlorobenzene.

In one particular exemplary embodiment, the reaction conditions for each reaction step is:

wherein, R is C1-20 saturated or unsaturated alkyl, or C1alkyl-unsubstituted or substituted alkylaryl. Preferably, wherein R is ethyl.

The compound of formula III is commercial available, or the compound of formula III can be prepared by the following reaction:

wherein, R is C1-20 saturated or unsaturated alkyl, or C1alkyl-unsubstituted or substituted aryl. The temperature the reaction is conducted is preferably in the range from 0° C. to 100° C. The base is present from about 1 to about 3 mole equivalents, compound II is present from about 1 to about 3 mole equivalents. Preferably, the reaction is conducted wherein the base is one or more of sodium, potassium or their corresponding bases. More preferably, the base is sodium methoxide, sodium ethoxide, sodium tert-butoxide or potassium tert-butoxide. The solvent is preferably selected from one or more of methanol, propanol or isopropanol.

In an exemplary embodiment of the present invention, the brivaracetam is synthesized using the following route:

In an exemplary embodiment of the present invention, the brivaracetam is synthesized using the following alternative routes:

Compared with other processes for making brivaracetam, the stereoselective method for the synthesis of brivaracetam of the present invention has the following benefits:

Raw materials are readily available and inexpensive.

Purification and isolation of the intermediate product are easy, sometimes by telescope reactions without purification.

The chiral center is from chiral starting materials, which is well defined. High quality material with high chiral purity is readily available. Optical purity is substantially maintained throughout the process.

The chiral purity of the product, brivaracetam, is very high. No chiral HPLC purification is needed.

The total yield of the process described herein is higher than the prior known processes. The total yield of the compound brivaracetam is more than 30% from the compound of formula I. In comparison, the total yield of the known processes in the prior art is about 15-20%. And the undesired isomer cannot be recycled and becomes a waste product that must be disposed of.

DETAILED DESCRIPTION OF THE PRESENTLY PREFERRED EMBODIMENTS

EXAMPLES

Example 1

Preparation of (1S,5R)-ethyl 2-oxo-3-oxabicyclo[3.1.0]hexane-1-carboxylate (III)

Figure 1:
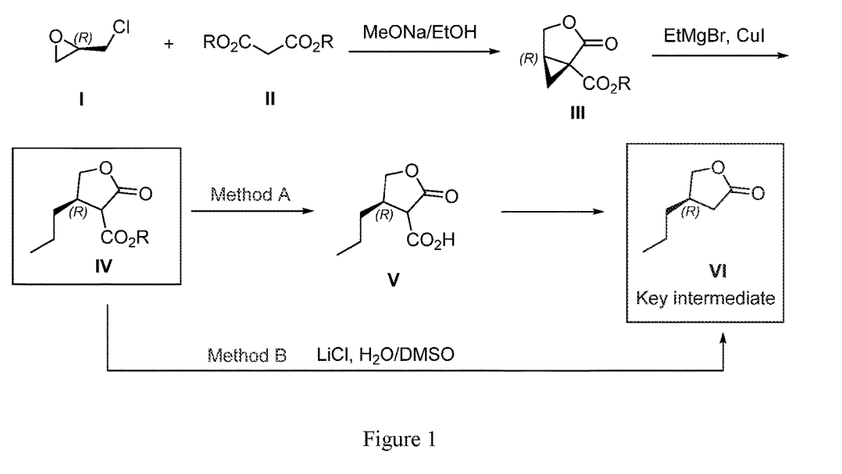
FIG. 1 depicts process routes to produce key intermediate VI, which are embodiments of the present invention. The processes use a commercial available and inexpensive chiral pool starting material (compound I). Compound IV and Compound IV are new compounds.
Figure 2:
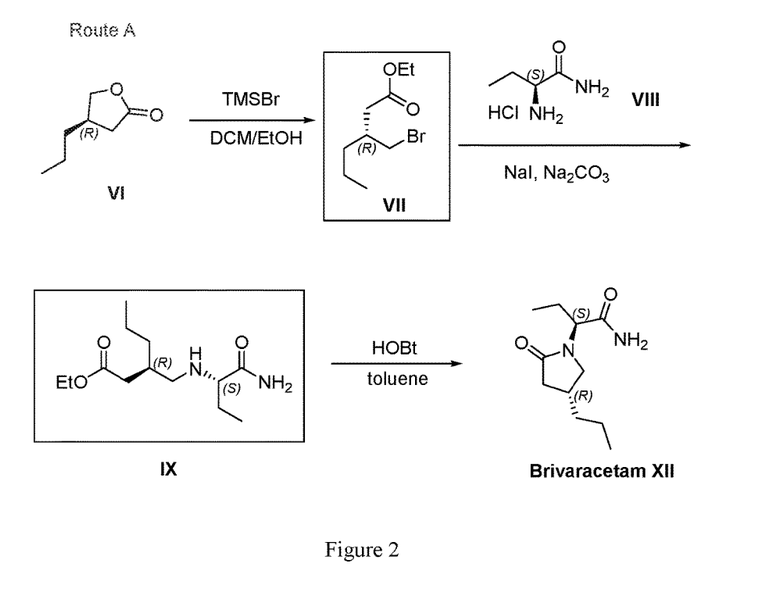
FIG. 2 depicts process routes to produce brivaracetam from the key intermediate VI, which are also embodiments of the present invention. Our synthesis (Route A) to brivaracetam comprises the making of intermediates of Compound VII and Compound IX, which are both novel. The Br in compound VII may also be another halogen, such as Cl or I, or OMs, OTs, ONs . The Et group in VII and IX may be H or C1-20 alkyl or C1alkyl-unsubstituted or substituted aryl.
Figure 3:
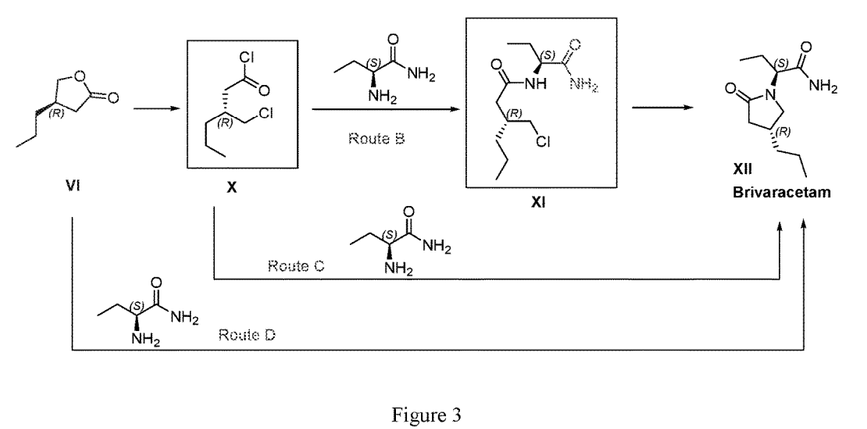
FIG. 3 depicts process routes to produce brivaracetam from the key intermediate VI, which are also embodiments of the present invention. Route B and Route C are our alternative synthesis to brivaracetam. Intermediate Compound X and Compound XI are new compounds. Route D may be conducted at high temperature and high pressure.

A mixture of sodium methoxide (2.05g, 38 mmol) and diethyl malonate (6.3 mL, 42 mmol) in ethanol (80 mL) was stirred at 0° C. for 10 min. (R)-(−)-epichlorohydrin (2.7 mL, 35 mmol) was added dropwise (over 20 min) at room temperature. The reaction mixture was then heated to reflux for 18 h. Upon reaction completion, the solvent was evaporated. The residue was dissolved in water (100 mL) and extracted with ethylacetate (3×100 mL). The organic layers were combined and dried over $Na_2SO_4$. Filtration and evaporation of the solvent afforded crude material, which was purified by vacuum distillation to obtain the title compound (1S,5R)-ethyl 2-oxo-3-oxabicyclo[3.1.0]hexane-1-carboxylate as a viscous colorless oil. Yield 55%, ee 98%.

$^1$H NMR (400MHz, $CDCl_3$) of the title compound: δ4.33 (1H, dd), 4.23 (2H, q), 4.16 (1H, d), 2.73-2.75 (1H, m), 2.05 (1H, dd), 1.35 (1H, t), 1.28 (3H,t).

Example 2

Preparation of (4R)-ethyl 4-propyl-2-oxotetrahydrofuran-3-carboxylate (IV)

To a stirred suspension of CuI (9.5 g, 50 mmol) in anhydrous THF at −30° C. was added ethyl magnesium bromide in THF (1.0 M, 300 mL, 300 mmol) dropwise. Stir at the same temperature for 1 h. A solution of compound III (20 g, 117 mmol) in anhydrous THF was added to the solution via cannula at −30° C. After stirred for 30 min, the reaction mixture was warmed to −15° C. and quenched with saturated ammonium chloride solution. The mixture was added water (1 L) and extracted with ethyl acetate (3×100 mL). The combined organic layers were dried over $Na_2SO_4$. Filtration and evaporation afforded crude product IV, which was purified by silica gel column chromatography using Petroleum ether/Ethylacetate (10:1) to obtain the title compound IV.

¹H NMR (400MHz, CDCl₃) of the title compound: δ4.52 (1H, dd), 4.27 (2H, q), 3.92 (1H, dd), 3.23 (1H, d), 2.96-3.03 (1H, m), 1.49-1.56 (2H, m), 1.27-1.35 (5H, m), 0.95 (3H,t).
$[α]^{23}_D$=+22.6 (C=10, CHCl₃)

Example 3

Preparation of (R)-4-propyldihydrofuran-2(3H)-one (VI)

The crude compound IV (about 117 mmol) and LiCl (14.7 g, 350 mmol) in DMSO/H2O (400 mL/20 mL) was heated for 18 h at 140° C. After the reaction was complete, water (400 mL) was added to the solution at room temperature. The solution was extracted with ethyl acetate (3×400 mL). The combined organic layers were washed with brine and dried over anhydrous Na₂SO₄. After evaporation of the solvent, the residue was purified by vacuum distillation to afford the title compound (R)-4-propyldihydrofuran-2(3H)-one (50% yield, yield for 2 steps) as a colorless oil.

¹H NMR (400 MHz, CDCl₃) of the title compound: δ4.42 (1H, dd), 3.92 (1H, dd), 2.52-2.65 (2H, m), 2.18 (1H, dd), 1.40-1.47 (2H, m), 1.40-1.47 (2H, m), 1.27-1.39 (2H, m), 0.94 (3H,t).
$[α]^{23}_D$=+3.9 (C=10, CHCl₃)

Example 4

Preparation of ethyl (R)-3-(bromomethyl)hexanoate (VII)

TMSBr (3.1 mL, 24 mmol) was added to a solution of the compound VI (1.1 g, 7.8mmol) and 2.5ml ethanol in dry DCM (40 mL) at 0° C. The solution was stirred at room temperature overnight. The reaction mixture was added Na₂S₂O₃ solution and water (50mL) and was extracted with ethyl acetate (3×50 mL). The combined organic layers were washed with brine and dried over anhydrous Na₂SO₄. After evaporation of the solvent, the residue was purified by silica gel column chromatography using petroleum ether/ethyl acetate (20:1) to afford the title compound VII, ethyl (R)-3-(bromomethyl)hexanoate as a colorless oil, yield 87%.

¹H NMR (400MHz, CDCl₃) of the title compound: δ 4.16 (q, 2H), 3.58 (dd, 1H),3.55 (dd, 1H), 2.51 (dd, 1H), 2.36 (dd, 1H), 2.15-2.30 (m, 1H), 1.25-1.51 (m, 7H), 0.94 (t, 3H).
$[α]^{23}_D$=−3.8 (C=10, CHCl₃)

Example 5

Preparation of ethyl (R)-3-((((S)-1-amino-1-oxobutan-2-yl)amino)methyl)hexanoate (IX)

Compound (S)-2-aminobutanamide hydrochloride (3.4g, 24.5 mmol), compound VII (2.83g, 20.4 mmol), Na₂CO₃ (7.78g, 73.4 mmol), and NaI (1.83g, 12.2mmol) were added to DMF (60 ml). The solution was stirred for 18 h at 90° C. After the reaction was complete, water (100 mL) was added to the solution at room temperature. The solution was extracted with ethyl acetate (3×50 mL). The combined organic layers were washed with brine and dried over anhydrous Na₂SO₄. Filtration and evaporation of the solvent afforded the crude product, which was purified by silica gel column chromatography using DCM/MeOH/TEA (100/1/1) to afford the title compound IX ethyl (R)-3-((((S)-1-amino-1-oxobutan-2-yl)amino)methyl)hexanoate (40% yield) as a yellow oil.

¹H NMR(400 MHz, CDCl₃) of the title compound: ¹H NMR (400 MHz, CDCl₃) δ 7.03 (brs, 1H), 5.86 (brs, 1H), 4.13 (q, 2H), 2.96 (t, 1H), 2.54 (dd, 1H), 2.33 (dd, 1H), 1.78-2.10 (m, 1H), 1.56-1.75 (m, 2 H), 1.24-1.48 (m, 7 H), 0.85-1.03 (m, 6H).

Example 6

Preparation of Brivaracetam (XII)

Compound IX (120 mg, 0.46 mmol) and HOBt (63 mg, 0.46 mmol) were added to toluene (1 ml). The solution was stirred for 3 h at 90° C. After the reaction was complete, saturated Na₂CO₃ solution (50 mL) was added to the reaction mixture at room temperature. The mixture was extracted with ethyl acetate (3×50 mL). The combined organic layers were washed with brine and dried over anhydrous Na₂SO₄. Filtration and evaporation of the solvent afforded the crude product, which was purified by silica gel column chromatography using EA/TEA (100/1) to afford the title compound XII brivaracetam (41% yield, 98% ee) as a white solid.

¹H NMR(400MHz, CDCl₃) of the title compound: δ 6.42 (brs, 1H), 5.69 (brs, 1H), 4.46 (dd, 1H), 3.50 (dd, 1H), 3.05 (dd, 1H), 2.57 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 7

Preparation of Brivaracetam (XII)

Compound IX (435 mg, 1.73 mmol) and 2-hydroxypyridine (82 mg, 0.86 mmol) were added to toluene (4 ml). The solution was stirred for 3 h at 90° C. After the reaction was complete, saturated Na₂CO₃ solution (50 mL) was added to the reaction mixture at room temperature. The mixture was extracted with ethyl acetate (3×50 mL). The combined organic layers were washed with brine and dried over anhydrous Na₂SO₄. Filtration and evaporation of the solvent afforded the crude product, which was purified by silica gel column chromatography using PE/EA/TEA (50/50/1) to afford the title compound XII brivaracetam (58% yield, 98% ee) as a white solid.

¹HNMR(400 MHz, CDCl₃) of the title compound:δ 6.42 (brs, 1 H), 5.69 (brs, 1 H), 4.46 (dd, 1H), 3.50 (dd, 1H), 3.05 (dd, 1H), 2.57 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 8

Preparation of Brivaracetam (XII)

Compound (S)-2-aminobutanamide hydrochloride (4.35 g, 31.5 mmol), compound VII (5.0 g, 21.0 mmol), Na₂CO₃ (8.9 g, 84.0 mmol) and NaI (1.57 g, 10.5 mmol) were added to DMF (50 ml). The solution was stirred for 18 h at 90° C. After the reaction was complete, water (100 mL) was added to the reaction mixture at room temperature. The mixture was extracted with ethyl acetate (3×50 mL) The combined organic layers were washed with brine and dried over anhydrous Na₂SO₄. The crude product and 2-hydroxypyridine (1.0 g, 10.5 mmol) were added to toluene (50 ml). The reaction mixture was stirred at 90° C. for 5 h. After the reaction was complete, saturated Na₂CO₃ solution (100 mL) was added to the reaction mixture at room temperature. The mixture was extracted with ethyl acetate (3×100 mL). The combined organic layers were washed with brine and dried over anhydrous $Na_2SO_4$. Filtration and evaporation of the solvent afforded the crude product, which was purified by silica gel column chromatography using PE/EA/TEA (50/50/1) to afford the title compound XII brivaracetam (50% yield, 98% ee) as a white solid.

$^1$H NMR(400 MHz, CDCl$_3$) of the title compound: δ 6.42 (brs, 1H), 5.69 (brs, 1H), 4.46 (dd, 1H), 3.50 (dd, 1H), 3.05 (dd, 1H), 2.57 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 9

Preparation of (R)-3-(chloromethyl)hexanoyl chloride (X)

A solution of thionyl chloride (20 mL), anhydrous ZnCl$_2$ (2.5 g, 18.3 mmol), and the compound of formula (VI) (12.0 g, 93.7 mmol) was stirred under 55° C. After the reaction was complete, the solvents were evaporated in vacuo and the residue was purified by vacuum distillation to obtain the title compound X as a yellow oil. Yield 68%.

$^1$H NMR(400MHz, CDCl$_3$) of the title compound: δ3.67 (1H, dd), 3.59 (1H, dd), 2.58 (1H, dd), 2.40 (1H, dd), 2.20-2.31 (1H, m), 1.25-1.53 (4H, m), 0.93 (3H, t).

$[α]^{23}_D$=+2.9 (C=10, CHCl$_3$)

Example 10

Preparation of (R)-3-(chloromethyl)hexanoyl chloride (X)

A solution of thionyl chloride (400 mL), anhydrous ZnCl$_2$ (40 g, 0.29 mol), and the compound of formula (VI) (188 g, 1.47 mol) was stirred at 85° C. After the reaction was complete by GC, the solvent was evaporated in vacuo and the residue was purified by vacuum distillation to obtain the title compound X as a yellow oil. Yield 63.5%.

$^1$H NMR(400 MHz, CDCl$_3$) of the title compound: δ3.67 (1H, dd), 3.59 (1H, dd), 2.58 (1H, dd), 2.40 (1H, dd), 2.20-2.31 (1H, m), 1.25-1.53 (4H, m), 0.93 (3H, t).

$[α]^{23}_D$=+2.9 (C=10, CHCl$_3$)

Example 11

Preparation of (R)-N-((S)-1-amino-1-oxobutan-2-yl)-3-(chloromethyl)hexanamide (XI)

Compound (S)-2-aminobutanamide hydrochloride (1.67 g, 12 mmol) was added to DCM (60ml). TEA (2.43 g, 24 mmol) was added to the solution at room temperature and stirred at room temperature for 30 min. Compound X (2.0 g, 10.8 mmol) was added to the solution. After the reaction was complete, water (30 ml) and ethanol (4 ml) was added to the solution. The mixture was extracted with DCM (2×40 mL). The combined organic layers were washed with brine and dried over anhydrous Na$_2$SO$_4$. Filtration and evaporation of the solvent afforded crude product of compound XI, yield 96.7%.

The crude product was purified by silica gel column chromatography using ethyl acetate, $^1$H NMR(400 MHz, CDCl$_3$) of the title compound: $^1$H NMR (400 MHz, CDCl$_3$) δ6.20-6.45 (2H, m), 5.69 (1H, brs), 4.46 (1H, dd), 3.61 (2H, d), 2.23-2.42 (3H, m), 1.85-1.97 (1H, m), 1.62-1.75 (1H, m), 1.23-1.53 (4H, m), 0.97 (3H, t), 0.91 (3H, t).

$[α]^{25}_D$=−23.7 (C=3, CH$_3$OH)

Example 12

Preparation of Brivaracetam (XII)

The crude product of compound XI (10.0 g, 40 mmol) were added to anhydrous THF (150 ml). t-BuOK (5.6 g, 50 mmol) was added to the reaction and cooled to −30° C. till TLC showed no starting material remained. After the reaction was complete, The saturated NH$_4$Cl solution (50 mL) was added to the solution. The solution was extracted with ethyl acetate (3×50 mL). The combined organic layers were washed with brine and dried over anhydrous Na$_2$SO$_4$. Filtration and evaporation of the solvent the crude product in 93% yield. Purified by recrystallization to afford the higher purity product (chiral HPLC>99.5%) as a white solid.

The $^1$H NMR(400 MHz, CDCl$_3$) of the title compound as follow: $^1$H NMR (400 MHz, CDCl$_3$) δ 6.45 (brs, 1H), 5.80 (brs, 1H), 4.47 (dd, 1H), 3.49 (dd, 1H), 3.06 (dd, 1H), 2.56 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 13

Preparation of Brivaracetam (XII)

To a solution of crude product of compound XI (10.0 g, 40 mmol) in DCM (150 ml), TBAC (2.3 g, 10 mmol) and anhydrous Na$_2$SO$_4$ (5.6 g, 40 mmol) were added. KOH (4.2 g, 75 mmol) was added at −10° C. After the reaction was complete, saturated NH$_4$Cl solution (50 mL) was added to quench the reaction. The reaction mixture was extracted with ethyl acetate (3×50 mL). The combined organic layers were washed with brine and dried over anhydrous Na$_2$SO$_4$. Filtration and evaporation of the solvent afforded crude brivaracetam in 96% yield. The crude product was purified by recrystallization to afford high purity product (chiral HPLC>99.5%) as a white solid.

$^1$H NMR(400 MHz, CDCl$_3$) of the title compound: $^1$H NMR (400 MHz, CDCl$_3$) δ 6.45 (brs, 1H), 5.80 (brs, 1H), 4.47 (dd, 1H), 3.49 (dd, 1H), 3.06 (dd, 1H), 2.56 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 14

Preparation of (R)-N-((S)-1-amino-1-oxobutan-2-yl)-3-(chloromethyl)hexanamide (XI)

Compound (S)-2-aminobutanamide hydrochloride (5.0 g, 36 mmol) and TEA (7.3 g, 72 mmol) were added to THF (100 ml) at room temperature. After 30 min, compound X (6.0 g, 32.5 mmol) was added. After the reaction was complete, water (100 ml) was added. The reaction mixture was extracted with EA (3×50 mL). The combined organic layers were washed with brineand dried over anhydrous Na$_2$SO$_4$. Filtration and evaporation of the solvent afforded, crude product of compound XI, which was purified by silica gel column chromatography using ethyl acetate as the eluent.

¹H NMR(400MHz, CDCl₃) of the title compound:δ6.20-6.45 (2H, m), 5.69 (1H, brs), 4.46 (1H, dd), 3.61 (2H, d), 2.23-2.42 (3H, m), 1.85-1.97 (1H, m), 1.62-1.75 (1H, m), 1.23-1.53 (4H, m), 0.97 (3H, t), 0.91 (3H, t).
$[\alpha]^{25}_D$=−23.7 (C=3, CH₃OH)

Example 15

Preparation of Brivaracetam (XII)

To a solution of the crude product of compound XI from example 14 in anhydrous THF (100 ml), t-BuOK (4.8 g, 43.2 mmol) was added. The solution was stirred for at 0° C. After the reaction was complete, saturated NH₄Cl solution (50 mL) was added. The reaction mixture was extracted with ethyl acetate (3×50 mL). The combined organic layers were washed with brine and dried over anhydrous Na₂SO₄. Filtration and evaporation of the solvent afforded crude brivaracetam, which was purified by recrystallization in IPAc to afford pure product (chiral HPLC>99.5%) as a white solid, yield 49% for 2 steps.

¹H NMR(400MHz, CDCl₃) of the title compound: δ 6.45 (brs, 1H), 5.80 (brs, 1H), 4.47 (dd, 1H), 3.49 (dd, 1H), 3.06 (dd, 1H), 2.56 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 16

Preparation of (R)-4-propyldihydrofuran-2(3H)-one (VI)

To a solution of sodium methoxide (2.05g, 38 mmol) in ethanol (80 mL) at 0° C., diethyl malonate (6.3 mL, 42 mmol) was added. The mixture was stirred at the same temperature for 10 min. (R)-(−)-epichlorohydrin (2.7 mL, 35 mmol) was added dropwise (over 20 min) at room temperature. The reaction mixture was heat to refluxed for 18 h. After the reaction was complete, the solvent was evaporated. The residue was added water (100 mL) and extracted with ethyl acetate (3×100 mL). The combined organic layers were dried over Na₂SO₄. Filtration and evaporation of solvent afforded the crude product, which was purified by vacuum distillation to obtain the compound III (1S,5R)-ethyl 2-oxo-3-oxabicyclo[3.1.0]hexane-1-carboxylate as a viscous colorless oil. Yield 55%, ee 98%.

To a stirred suspension of CuI (9.5 g, 50 mmol) in anhydrous THF at −30° C. was added ethyl magnesium bromide in THF (1.0 M, 300 mL, 300 mmol) dropwise. After 1 h, a solution of compound III (20 g, 117 mmol) in anhydrous THF was added via cannula at −30° C. The reaction mixture was warmed to −15° C. before quenched with saturated ammonium chloride solution. The mixture was added water (100 mL) and extracted with ethyl acetate (3×100 mL). The combined organic layers were dried over Na₂SO₄. Filtration and evaporation of solvent afforded the crude product IV.

The crude product of compound IV (about 117 mmol) and LiCl (14.7 g, 350 mmol) in DMSO/H₂O (400 mL/20 mL) was heated for 18 h at 140° C. After the reaction was complete, water (400 mL) was added to the solution at room temperature. The reaction mixture was extracted with ethyl acetate (3×400mL). The combined organic layers were washed with brine and dried over anhydrous Na₂SO₄. Filtration and evaporation of the solvent afforded the crude product, which was purified by vacuum distillation to afford the title compound VI (R)-4-propyldihydrofuran-2(3H)-one (50% yield, yield for 2 steps) as a colorless oil.

¹H NMR(400 MHz, CDCl₃) of the title compound: δ4.42 (1H, dd), 3.92 (1H, dd), 2.52-2.65 (2H, m), 2.18 (1H, dd), 1.40-1.47 (2H, m), 1.40-1.47 (2H, m), 1.27-1.39 (2H, m), 0.94 (3H,t).
$[\alpha]^{23}_D$=+3.9 (C=10, CHCl₃)

Example 17

Preparation of (1S,5R)-ethyl 2-oxo-3-oxabicyclo [3.1.0]hexane-1-carboxylate (III)

Sodium methoxide (2.0 kg, 37.03 mol) was dissolved in ice cold ethanol (44.5 kg) and stirred for 15 min. The resulting mixture was added diethyl malonate (6.0 kg, 37.46 mol) at 10° C. and was stirred at the same temperature for 10 min. (R)-(−)-epichlorohydrin (3.3 mL, 35.67 mol) was added dropwise (over 20 min) at the room temperature. After refluxing for 2 h, the solvent was evaporated. The residue was added water (19.3 kg) and was extracted with ethyl acetate twice (17.0 kg and 12.0 kg). The combined organic layers were dried over Na₂SO₄. Filtration and evaporation of solvent afforded the crude product, which was purified by vacuum distillation to obtain the title compound III as a viscous colorless oil. Yield 50%, ee 98.5%

¹H NMR(400 MHz, CDCl₃) of the title compound: ¹H NMR(400MHz, CDCl₃): δ4.33 (1H, dd), 4.23 (2H, q), 4.16 (1H, d), 2.73-2.75 (1H, m), 2.05 (1H, dd), 1.35 (1H, t), 1.28 (3H, t).

Example 18

Preparation of (4R)-ethyl 4-isobutyl-2-oxotetrahydrofuran-3-carboxylate (IV)

CuI (108.3 g, 0.57 mol) was added to a stirred suspension of ethyl magnesium bromide in 2-Me-THF (1.29 mol/kg, 2.44 kg, 3.14 mol) at −20 to −30° C. After 0.5 h, a solution of compound III (434 g, 2.55 mol) in anhydrous 2-Me-THF was added at −30° C. After 30 min, the reaction mixture was quenched with saturated ammonium chloride solution. Layers separation afforded a solution of the crude compound IV in 2-Me-THF. Yield 64%.

The crude product was purified by silica gel column chromatography using petroleum ether/ethyl acetate (10:1) to obtain the title compound IV.

¹H NMR(400 MHz, CDCl₃) of the title compound: δ4.52 (1H, dd), 4.27 (2H, q), 3.92 (1H, dd), 3.23 (1H, d), 2.96-3.03 (1H, m), 1.49-1.56 (2H, m), 1.27-1.35 (5H, m), 0.95 (3H,t).
$[\alpha]^{23}_D$=+22.6 (C=10, CHCl₃)

Example 19

Preparation of (4R)-ethyl 4-isobutyl-2-oxotetrahydrofuran-3-carboxylate (IV)

CuI (2.22 g, 11.70 mmol) was added to a stirred suspension of ethyl magnesium bromide in 2-Me-THF (1.29 mol/kg, 63.51 g, 81.93 mmol) at −20 to −30° C. After 0.5 h, a solution of compound III (10.0 g, 58.52 mol) in anhydrous 2-Me-THF was added at −30° C. After 30 min, the reaction was quenched with saturated ammonium chloride solution. then the residue was stirred for 30 min. Layers separation afforded a solution of the crude compound IV in 2-Me-THF. Yield 87%.

The crude product was purified by silica gel column chromatography using petroleum ether/ethyl acetate (10:1) to obtain the title compound IV.

$^1$H NMR(400 MHz, CDCl$_3$) of the title compound: δ4.52 (1H, dd), 4.27 (2H, q), 3.92 (1H, dd), 3.23 (1H, d), 2.96-3.03 (1H, m), 1.49-1.56 (2H, m), 1.27-1.35 (5H, m), 0.95 (3H,t).

$[\alpha]^{23}_D$=+22.6 (C=10, CHCl$_3$)

Example 20

Preparation of (4R)-2-oxo-4-propyltetrahydrofuran-3-carboxylic acid

To a suspension of crude product of compound IV in 2-Me-THF (from example 19) at 25 to 30° C., NaOH/H$_2$O (255 g/640 ml) was added. After 2 h, the mixture was wash with ethyl acetate (1 L). The pH of the mixture was adjusted to pH=1 with concentrated HCl, and was extracted with 2-Me-THF (2×1 L). The combined organic layers were concentrated to give the crude product. Yield 99%.

The crude product was purified by silica gel column chromatography using 100% ethyl acetate.

$^1$H NMR(400MHz, CDCl$_3$) of the title compound:δ10.57 (1H, brs), δ4.54 (1H, dd), 3.95 (1H, dd), 3.30 (1H, d), 2.96-3.03 (1H, m), 1.39-1.76 (2H, m), 1.27-1.35 (2H, m), 0.95 (3H, t).

Example 21

Preparation of (R)-4-propyldihydrofuran-2(3H)-one (VI)

The crude product of (4R)-2-oxo-4-propyltetrahydrofuran-3-carboxylic acid (from example 20) in toluene was heated at 120° C. for 2 h. After the reaction was complete, the mixture was purified by vacuum distillation to afford the title compound (R)-4-propyldihydrofuran-2(3H)-one (99% yield).

$^1$H NMR(400 MHz, CDCl$_3$) of the title compound: δ4.42 (1H, dd), 3.92 (1H, dd), 2.52-2.65 (2H, m), 2.18 (1H, dd), 1.40-1.47 (2H, m), 1.40-1.47 (2H, m), 1.27-1.39 (2H, m), 0.94 (3H,t).

$[\alpha]^{23}_D$=+3.9 (C=10, CHCl$_3$)

Example 22

Preparation of (R)-4-propyldihydrofuran-2(3H)-one (VI)

The crude product of (4R)-2-oxo-4-propyltetrahydrofuran-3-carboxylic acid (from example 20) and toluene (2 vol) was heated at 120° C. for 8 h. After the reaction was complete, the mixture was purified by vacuum distillation to afford the title compound (R)-4-propyldihydrofuran-2(3H)-one (95% yield).

$^1$H NMR(400 MHz, CDCl$_3$) of the title compound: δ4.42 (1H, dd), 3.92 (1H, dd), 2.52-2.65 (2H, m), 2.18 (1H, dd), 1.40-1.47 (2H, m), 1.40-1.47 (2H, m), 1.27-1.39 (2H, m), 0.94 (3H,t).

$[\alpha]^{23}_D$=+3.9 (C=10, CHCl$_3$)

Example 23

Preparation of (R)-3-(chloromethyl)hexanoyl chloride (X)

A solution of thionyl chloride (200 mL), anhydrous ZnCl$_2$ (10.6 g, 0.078 mol), and the compound of formula (VI) (100 g, 0.78 mmol) was heated to 85° C. After the reaction was complete, the solvents were evaporated in vacuo. The crude product was purified by vacuum distillation to obtain the title compound X as a yellow oil. Yield 79.7%.

$^1$H NMR(400 MHz, CDCl$_3$) of the title compound: δ3.67 (1H, dd), 3.59 (1H, dd), 2.58 (1H, dd), 2.40 (1H, dd), 2.20-2.31 (1H, m), 1.25-1.53 (4H, m), 0.93 (3H, t).

$[\alpha]^{23}_D$=+2.9 (C=10, CHCl$_3$)

Example 24

Preparation of (R)—N—((S)-1-amino-1-oxobutan-2-yl)-3-(chloromethyl)hexanamide (XI)

To a mixture of (S)-2-aminobutanamide hydrochloride (10.0 g, 72.5 mmol) and K$_2$CO$_3$ (25 g, 181.3 mmol) in CH$_3$CN (150 ml) at 0° C., the compound of formula (X) (14.6 g, 79.71 mmol) was added. After the reaction was complete by TLC, the solvents were evaporated in vacuo. DCM (150 ml), water (150 ml), and ethanol (10 ml) was added. Layers were separated. The aqueous layer was extracted with DCM (100 ml). The combined organic layers were dried over anhydrous Na$_2$SO$_4$. Filtration and evaporation of the solvent afforded crude compound XI, yield 96%.

the crude compound (XI) was purified by recrystallization to afford the high purity product as a white solid.

$^1$H NMR(400 MHz, CDCl$_3$) of the title compound: 6.20-6.45 (2H, m), 5.69 (1H, brs), 4.46 (1H, dd), 3.61 (2H, d), 2.23-2.42 (3H, m), 1.85-1.97 (1H, m), 1.62-1.75 (1H, m), 1.23-1.53 (4H, m), 0.97 (3H, t), 0.91 (3H, t).

$[\alpha]^{25}_D$=−23.7 (C=3, CH$_3$OH)

Example 25

Preparation of Brivaracetam (XII)

To a solution of compound XI (2.0 g, 8 mmol) in anhydrous DMF (6 ml), KOH (670 mg, 12 mmol) was added portionwise at −15° C. to −10° C. After the reaction was complete by HPLC, the reaction was quenched with 1N HCl. Brine (24 ml) were added. The mixture was extracted with MTBE (4×20 mL). The combined organic layers were washed with brine and dried over anhydrous Na$_2$SO$_4$. Filtration and evaporation of the solvent gave crude brivaracetam, yield 95%. Recrystallization afforded pure product (chiral HPLC>99.5%) as a white solid.

$^1$H NMR(400 MHz, CDCl$_3$) of the title compound: δ 6.45 (brs, 1H), 5.80 (brs, 1H), 4.47 (dd, 1H), 3.49 (dd, 1H), 3.06 (dd, 1H), 2.56 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 26

Preparation of Brivaracetam (XII)

To a mixture of (S)-2-aminobutanamide hydrochloride (8.0 g, 58 mmol) and PEG400 (3.5 g, 8.7 mmol) in DCM (120 ml) at -10° C., compound X (11.7 g, 645 mmol) and KOH (17.9g, 320mmol) were added portionwise. The reaction was stirred at 2° C. reaction completion by TLC. A solution of half saturated NH$_4$Cl was added. The mixture was extracted with DCM (3×40 mL). The combined organic layerers were washed with brine and dried over anhydrous Na$_2$SO$_4$. Filtration and evaporation of solvent gave crude brivaracetam, yield 95%. Recrystallization afforded pure product (chiral HPLC>99%) as a white solid.

$^1$H NMR(400MHz, CDCl$_3$) of the title compound: δ 6.45 (brs, 1H), 5.80 (brs, 1H), 4.47 (dd, 1H), 3.49 (dd, 1H), 3.06 (dd, 1H), 2.56 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 27

Preparation of Brivaracetam (XII)

To a mixture of (S)-2-aminobutanamide hydrochloride (2.5 g, 18 mmol) and TBAB (1.16 g, 3.6 mmol) in DCM (40 ml) at −10° C., compound X (3.66 g, 20 mmol) and KOH (4.53g, 81 mmol) were added portionwise. The reaction was stirred at −2° C. till completion by TLC. A solution of half saturated NH$_4$Cl was added. The mixture was extracted with DCM (3×40 mL). The combined organic layers were washed with brine and dried over anhydrous Na$_2$SO$_4$. Filtration and evaporation of solvent gave crude brivaracetam, yield 83%. Recrystallization afforded pure product (chiral HPLC>99%) as a white solid.

$^1$H NMR(400 MHz, CDCl$_3$) of the title compound: δ 6.45 (brs, 1H), 5.80 (brs, 1H), 4.47 (dd, 1H), 3.49 (dd, 1H), 3.06 (dd, 1H), 2.56 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 28

Preparation of Brivaracetam (XII)

To a solution of compound XI (2.5 g, 10 mmol) and TBAB (161 mg, 0.5 mmol) in anhydrous DCM (20 ml), KOH (730 mg, 12 mmol) was added in two portions. The reaction was stirred for at −15° C. to −10° C. till reaction completion by HPLC. A saturated NH$_4$Cl solution was added. The mixture was extracted with DCM three times. The combined organic layers were washed with brine and dried over anhydrous Na$_2$SO$_4$. Filtration and evaporation of solvent gave crude brivaracetam, yield 68%. Recrystallization afforded pure product (chiral HPLC>99.5%) as a white solid.

$^1$H NMR(400 MHz, CDCl$_3$) of the title compound: δ 6.45 (brs, 1H), 5.80 (brs, 1H), 4.47 (dd, 1H), 3.49 (dd, 1H), 3.06 (dd, 1H), 2.56 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 29

Preparation of Brivaracetam (XII)

To a solution of compound XI (100 mg, 0.4 mmol) and PEG400 (24 mg, 0.06 mmol) in anhydrous DCM (1 ml), NaOH (32 mg, 0.8 mmol) was added. The reaction was stirred at −15° C. to −10° C. till reaction completion by HPLC. A saturated NH$_4$Cl solution was added. The mixture was extracted with DCM three times. The combined organic layers were washed with brine and dried over anhydrous Na$_2$SO$_4$. Filtration and evaporation of solvent afforded brivaracetam, yield 87%.

$^1$H NMR(400 MHz, CDCl$_3$) of the title compound: δ 6.45 (brs, 1H), 5.80 (brs, 1H), 4.47 (dd, 1H), 3.49 (dd, 1H), 3.06 (dd, 1H), 2.56 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 30

Preparation of Brivaracetam (XII)

To a mixture of compound XI (100 mg, 0.4 mmol) and PEG400 (24 mg, 0.06 mmol) in anhydrous CH$_3$CN (1 ml) was added KOH (45 mg, 0.8 mmol). The reaction was stirred at −15° C. to −10° C. till reaction completion by HPLC. A saturated NH$_4$Cl solution was added. The mixture was extracted with DCM three times. The combined organic layer were washed with brine and dried over anhydrous Na$_2$SO$_4$. Filtration and evaporation of solvent afforded brivaracetam, yield 86%.

$^1$H NMR(400 MHz, CDCl$_3$) of the title compound: δ 6.45 (brs, 1H), 5.80 (brs, 1H), 4.47 (dd, 1H), 3.49 (dd, 1H), 3.06 (dd, 1H), 2.56 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 31

Preparation of Brivaracetam (XII)

To a solution of compound XI (100 mg, 0.4 mmol) and PEG400 (24 mg, 0.06 mmol) in acetone (1 ml) was added KOH (45 mg, 0.8 mmol). The mixture was stirred at −15° C. to −10° C. till reaction completion by HPLC. A saturated NH$_4$Cl solution was added. The mixture was extracted with DCM three times. The combined organic layers were washed with brine and dried over anhydrous Na$_2$SO$_4$. Filtration and evaporation of solvent afforded brivaracetam, yield 90%.

The result of $^1$H NMR(400MHz, CDCl$_3$) analysis of the title compound as follow: $^1$H NMR (400 MHz, CDCl$_3$) δ 6.45 (brs, 1H), 5.80 (brs, 1H), 4.47 (dd, 1H), 3.49 (dd, 1H), 3.06 (dd, 1H), 2.56 (dd, 1H), 2.25-2.40 (m, 1H), 2.05 (dd, 1H), 1.78-1.99 (m, 1H), 1.54-1.75 (m, 1H), 1.25-1.48 (m, 4 H), 0.80-0.95 (m, 6H).

Example 32

Preparation of (R)-4-propyldihydrofuran-2(3H)-one (VI)

To a suspension of CuI (9.5 g, 50 mmol) in anhydrous THF at −30° C. was added ethyl magnesium bromide in THF (1.0 M, 300 mL, 300 mmol) dropwise. After 1 h, a solution of compound III (20 g, 117 mmol) in anhydrous THF was added via cannula at −30° C. After 30 min, the reaction mixture was warmed to −15° C. and quenched with saturated ammonium chloride solution. The mixture was added water (100 mL) and extracted with ethyl acetate (3×100 mL). The combined organic layers were dried over Na$_2$SO$_4$. Filtration and evaporation of solvent afforded crude product (IV).

The crude product of compound IV (about 117 mmol) and LiCl (14.7 g, 350 mmol) in DMSO/H$_2$O (400 mL/20 mL) was heated at 140° C. for 18 h. After the reaction was complete, water (400 mL) was added at room temperature. The mixture was extracted with ethyl acetate (3×400mL). The combined organic layers were washed with brine and dried over anhydrous Na$_2$SO$_4$. Filtration and evaporation of solvent afforded crude product, which was purified by

Example 33

Preparation of (4R)-2-oxo-4-propyltetrahydrofuran-3-carboxylic acid

CuI (2.24 g, 11.79 mmol) was added to a suspension of ethyl magnesium bromide in 2-Me-THF (1.36 mol/kg, 64.85 g, 88.2 mmol) at −20 to −30° C. After 0.5 h, a solution of compound III (10.0 g, 58.52 mol) in anhydrous 2-Me-THF was added at −30° C. After 30 min, the reaction was quenched with 3N HCl solution. The reaction mixture was heated to reflux for 24 h. The layers were separated after cooling down to room temperature. The organic layer contained the crude 4R)-2-oxo-4-propyltetrahydrofuran-3-carboxylic acid. Yield 74%.

The crude 4R)-2-oxo-4-propyltetrahydrofuran-3-carboxylic acid was purified by silica gel column chromatography using 100% ethyl acetate $^1$H NMR(400 MHz, CDCl$_3$) of the title compound:δ10.57 (1H, brs), δ4.54 (1H, dd), 3.95 (1H, dd), 3.30 (1H, d), 2.96-3.03 (1H, m), 1.39-1.76 (2H, m), 1.27-1.35 (2H, m), 0.95 (3H, t).

Example 34

Preparation of (R)-4-propyldihydrofuran-2(3H)-one (VI)

CuI (2.24 g, 11.79 mmol) was added to a suspension of ethyl magnesium bromide in 2-Me-THF (1.36 mol/kg, 64.85 g, 88.2 mmol) at −20 to −30° C. After 0.5 h, a solution of compound III (10.0 g, 58.52 mol) in anhydrous 2-Me-THF was added at −30° C. After 30 min, the reaction was quenched with saturated ammonium chloride solution (50 ml). The layers were separated. NaOH/H$_2$O (7 g/18 ml) was added to the organic layer at 25 to 30° C. After 2 h, layers were separated. The aqueous was extracted with 2-Me-THF (50 mL). The combined organic layers were added concentrated HCl to pH=1. The mixture was extracted with 2-Me-THF twice. The organic layers were combined and the solvent was evaporated. The residue was heated to 105° C. for 10 h till reaction completion. Vacuum distillation afford the title compound (VI). (75% yield).

$^1$H NMR(400 MHz, CDCl$_3$) of the title compound: δ4.42 (1H, dd), 3.92 (1H, dd), 2.52-2.65 (2H, m), 2.18 (1H, dd), 1.40-1.47 (2H, m), 1.40-1.47 (2H, m), 1.27-1.39 (2H, m), 0.94 (3H,t).

$[\alpha]^{23}_D$=+3.9 (C=10, CHCl$_3$)

The following two Examples depict certain steps of the below scheme:

R=OMe

Example 35

Preparation of methyl (S)-2-((R)-3-(chloromethyl) hexanamido)butanoate (XI-a)

To a mixture of methyl (S)-2-aminobutanoate hydrochloride (5.0 g, 32.6 mmol) and K$_2$CO$_3$ (11.2 g, 81.7 mmol) in acetone (100 ml) at 0° C., compound X (6.28 g, 34.3 mmol) was added. After the reaction was complete by TLC, the solvents were evaporated in vacuo. The residue was added DCM (50 ml) and water (50 ml). The layers were separated. The aqueous layer was extracted with DCM (50 ml). The combined organic layers were dried over anhydrous Na$_2$SO$_4$. Filtration and evaporation of the solvent afforded crude compound XI-a (R=OMe), which was purified by silica gel column chromatography using PE/EA (20/1) to afford the title compound XI-a (R=OMe, 70% yield).

$^1$H NMR(400 MHz, CDCl$_3$) of the title compound: δ 6.24 (1H, d), 4.54 (1H, ddd), 3.72 (3H, s), 3.61 (2H, d), 2.23-2.42 (3H, m), 1.85-1.95 (1H, m), 1.62-1.75 (1H, m), 1.23-1.53 (4H, m), 0.85-0.95 (6H, m).

Example 36

Preparation of methyl (S)-2-((R)-2-oxo-4-propylpyrrolidin-1-yl)butanoate (XII-a, R=OMe)

R = OMe

To a solution of compound XI-a (R=OMe, 2.0 g, 7.6 mmol) in anhydrous DMF (6 ml), KOH (670 mg, 12 mmol) was added portionwise at −15° C. to −10° C. After the reaction was complete by HPLC, the reaction was quenched with 1N HCl. Brine (24 ml) were added. The mixture was extracted with MTBE (4×20 mL). The combined organic layers were washed with brine and dried over anhydrous Na$_2$SO$_4$. Filtration and evaporation of the solvent gave crude compound XII-a, which was purified by silica gel column chromatography using PE/EA (15/1) to afford the title compound XII-a (65% yield).

$^1$H NMR(400 MHz, CDCl$_3$) of the title compound: δ 4.67 (dd, 1H), 3.69 (s, 3H), 3.40 (dd, 1H), 3.12 (dd, 1H), 2.53 (dd, 1H), 2.32-2.40 (m, 1H), 2.05 (dd, 1H), 1.95-2.05 (m, 1H), 1.62-1.75 (m, 1H), 1.25-1.48 (m, 4 H), 0.85-0.95 (m, 6H).

The invention is not limited by the embodiments described above which are presented as examples only but can be modified in various ways within the scope of protection defined by the appended patent claims.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A process for the preparation of the compound of formula XII from the compound of formula IV, wherein, R is saturated or unsaturated C1-20 alkyl or C1alkyl-unsubstituted or substituted aryl, comprising the steps of decarboxylation of the compound of formula IV to produce the compound of formula VI ring-opening of the compound of formula VI to produce the compound of formula VII wherein R1 is saturated or unsaturated C1-20 alkyl or C1alkyl-unsubstituted or substituted aryl;

and X is Cl, Br, I, OMs, OTs, ONs; or the compound of formula X then converting VII or X by reacting with (S)-2-aminobutanamide or its salt or alkyl (S)-2-aminobutanoate to produce the compound of formula XII, or reacting the compound of formula VI with (S)-2-aminobutanamide or its salt to produce the compound of formula XII in one step; or reacting the compound of formula VI with alkyl (S)-2-aminobutanoate to produce XII-a wherein R in the compound of formula XII-a is a saturated or unsaturated C1-C20 alkoxyl ; and
then converting XII-a to XII by aminolysis and amide formation reaction.

2. The process of claim 1 where the compound of formula IV is converted to the compound of formula VI as follows:

a) the compound of formula IV is converted to the compound of formula VI in the presence of a solvent and a salt or base; and wherein R is C1-20 saturated or unsaturated alkyl; or
b) the compound of formula IV is converted to the compound of formula V which in turn is converted to compound of formula VI.

3. A process of claim 1 wherein the preparation of VII from VI comprises the step of
a) converting the compound of the formula VI to the compound of formula VII in the presence of a solvent and TMSI, TMSBr, HBr, HCl or HI; or
b) ring-opening of the compound of the formula VI and hydrolysis under basic conditions in a solvent, followed by esterification and a reaction with sulfonyl chloride, wherein the sulfonyl chloride is selected from the group consisting of MsCl, TsCl, and NsCl, to obtain the compound of formula VII;
wherein R1 is saturated or unsaturated C1-20 alkyl or C1alkyl-unsubstituted or substituted aryl;
and X is Cl, Br, I, OMs, OTs, or ONs.

4. A process of claim 1 wherein brivaracetam XII is prepared from VII wherein R1 is saturated or unsaturated C1-20 alkyl or C1alkyl-unsubstituted or substituted aryl;
and X is Cl, Br, I, OMs, OTs, ONs.

5. The process of claim 4

-continued

IX

IX-a comprising reacting the compound of formula VII with (S)-2-aminobutanamide or its salt or alkyl (S)-2-aminobutanoate in a solvent under basic conditions to produce the compound of formula IX or IX-a, and converting the compound of formula IX or IX-a to XII.

6. A process of claim 1 wherein the compound of formula X is prepared from the compound of formula VI comprising the step of reacting the compound of VI with SOCl2 and a Lewis acid catalyst to produce the compound of formula X.

7. A process of claim 1 wherein the compound of formula XII (brivaracetam) is produced from the compound of formula X 8. The process of claim 7, comprising the step of reacting the compound of Formula X with (S)-2-aminobutanamide or its salt to produce the compound of formula XII (brivaracetam); or reacting the compound of Formula X with alkyl (S)-2-aminobutanoate to produce the compound of formula XII-a, followed by aminolysis or hydrolysis/amide formation to produce the compound of formula XII (brivaracetam), wherein R is NH2, C1-C20 alkoxyl; if R is NH2, XII-a is XII; or or reacting the compound of Formula X with alkyl (S)-2-aminobutanoate to produce the compound of formula XI-a; and converting the compound of formula XI-a to the compound of XII-a; then converting the compound of XII-a to XII

XI-a

XII-a wherein R is NH₂, C1-C20 alkoxyl; if R is NH2, then XI-a is XI, and XII-a is XII.

9. A process of claim 1 for preparation of the compound of formula XII (brivaracetam), which comprises the steps of:

10. A process of claim 1 for preparation of the compound of formula XII (brivaracetam), which comprises the step of:

11. A process of claim 1 for preparation of the compound of formula XII (brivaracetam), which comprises the step of the reacting the compound of formula VI with (S)-2-aminobutanamide to produce the compound of formula XII (brivaracetam).

* * * * *